(12) United States Patent
Bone et al.

(10) Patent No.: US 9,993,499 B2
(45) Date of Patent: Jun. 12, 2018

(54) PRODUCT FOR AND METHOD OF PROTECTING AND INCREASING FRICTION OF ANIMAL PAWS

(71) Applicants: Stacey Bone, Des Peres, MO (US); Jeffrey L. Harms, Maplewood, MO (US)

(72) Inventors: Stacey Bone, Des Peres, MO (US); Jeffrey L. Harms, Maplewood, MO (US)

(*) Notice: Subject to any disclaimer, the term of this patent is extended or adjusted under 35 U.S.C. 154(b) by 0 days. days.

(21) Appl. No.: 15/061,058

(22) Filed: Mar. 4, 2016

(65) Prior Publication Data

US 2017/0119812 A1    May 4, 2017

Related U.S. Application Data

(60) Provisional application No. 62/128,122, filed on Mar. 4, 2015.

(51) Int. Cl.

| A61K 31/785 | (2006.01) |
| A01K 29/00 | (2006.01) |
| C09J 5/00 | (2006.01) |
| C09J 9/00 | (2006.01) |
| C09J 11/08 | (2006.01) |
| C09J 135/04 | (2006.01) |
| C09K 3/14 | (2006.01) |
| C09J 4/00 | (2006.01) |

(52) U.S. Cl.
CPC ............ *A61K 31/785* (2013.01); *A01K 29/00* (2013.01); *C09J 4/00* (2013.01); *C09J 5/00* (2013.01); *C09J 9/00* (2013.01); *C09J 11/08* (2013.01); *C09J 135/04* (2013.01); *C09K 3/149* (2013.01); *C09J 2433/00* (2013.01)

(58) Field of Classification Search
CPC . A01K 13/007; A01L 3/00; A01L 3/02; A01L 3/06; A01L 7/00; A01L 7/04; A01L 7/06; A01L 9/00; A01L 15/00; C09K 3/14; C09K 3/149
See application file for complete search history.

(56) References Cited

U.S. PATENT DOCUMENTS

| 4,444,933 A * | 4/1984 | Columbus ............. C08F 259/04 |
| | | 524/292 |
| 6,231,972 B1 * | 5/2001 | Fryer ...................... A01L 15/00 |
| | | 428/343 |

FOREIGN PATENT DOCUMENTS

WO    WO 2005082133 A1 *  9/2005   ........... A01K 13/006

OTHER PUBLICATIONS

English machine translation of WO2005082133A1 made Jun. 21, 2017.*

* cited by examiner

*Primary Examiner* — Michael B. Pallay
(74) *Attorney, Agent, or Firm* — Linda L. Lewis; Dennis Donahue; CreatiVenture Law

(57) ABSTRACT

An adhesive and solid particulates adhered to the pads of an animal's paw, the adhesive being cured, thereby increasing the friction of the surface of the pads; and a method of increasing the friction of an animal's paw by applying to clean, dry pads of the animal's paw a layer of uncured adhesive, and while the adhesive layer is uncured, contacting the paw with particulates to adhere the particulates to the pad, then curing the adhesive.

12 Claims, 9 Drawing Sheets

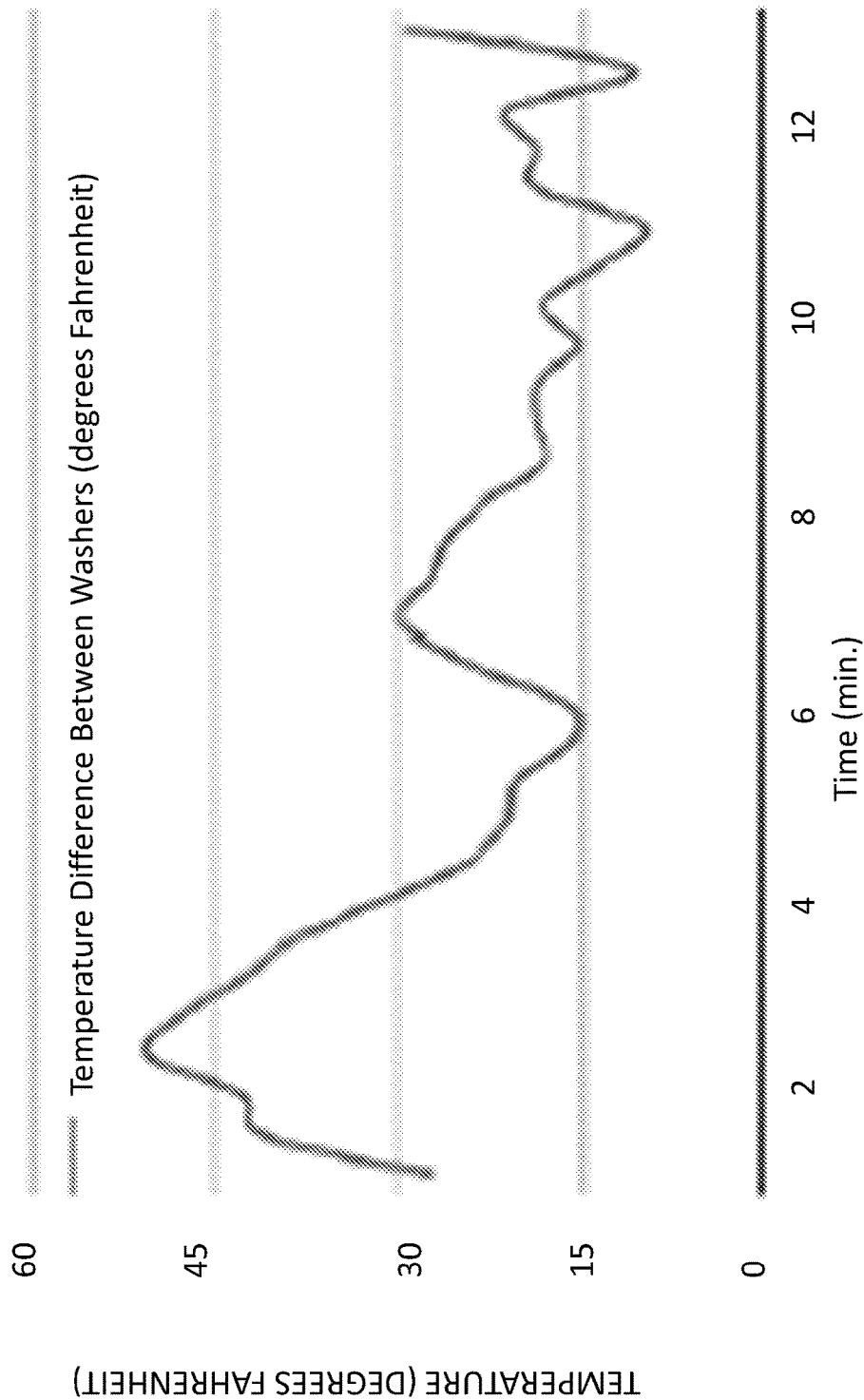

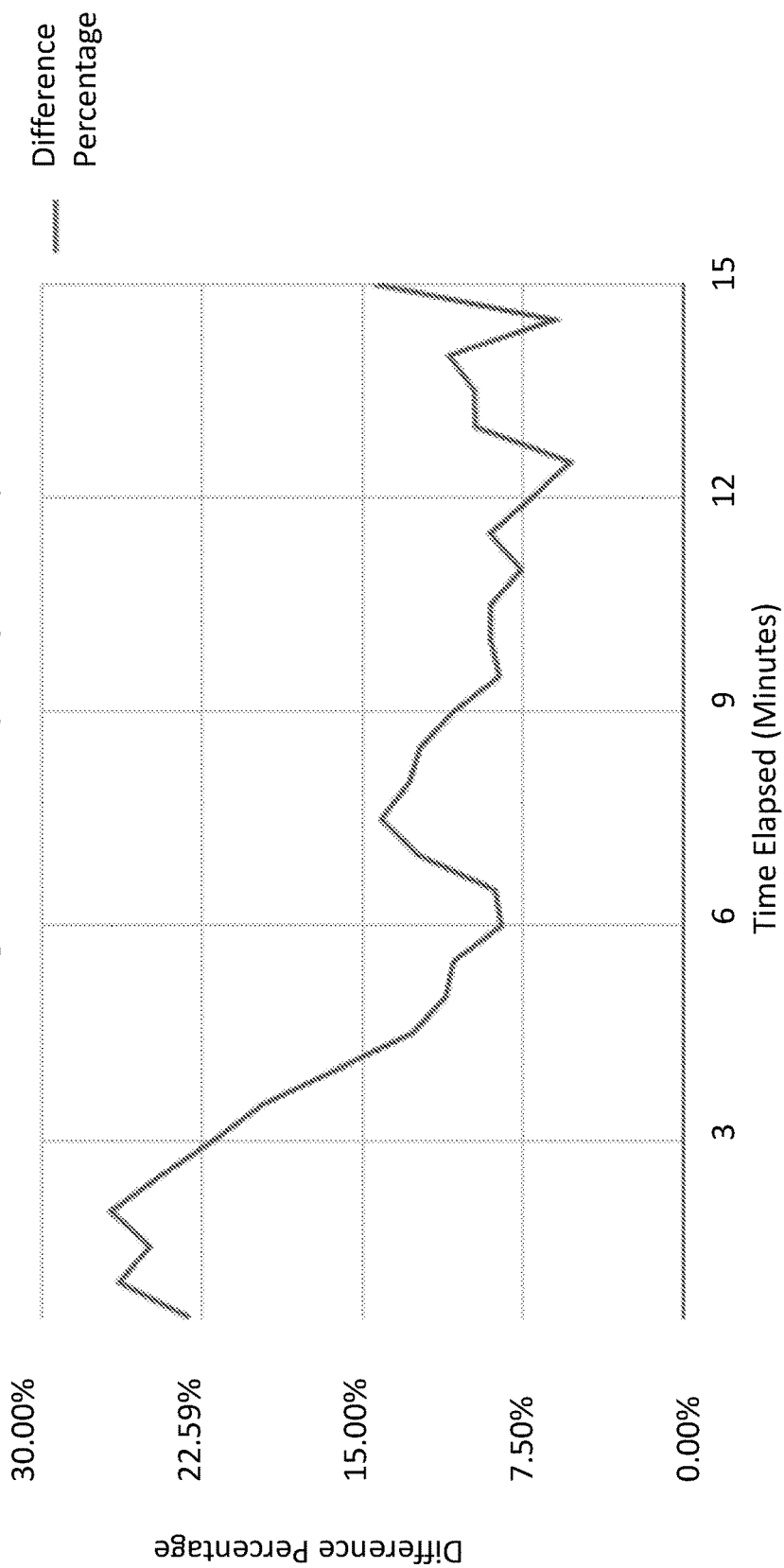

PRODUCT FOR AND METHOD OF PROTECTING AND INCREASING FRICTION OF ANIMAL PAWS

CROSS-REFERENCE TO RELATED APPLICATIONS

This application is claims the benefit of Provisional Patent Application Ser. No. 62/128,122 filed Mar. 4, 2015, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to a method of and product for protecting and increasing the friction of animal paws, and more particularly to adhering a granulated solid directly to the pads of an animal paw or paws to protect and increase friction.

Related Art

With the aging pet population and the propensity for homeowners to install hardwood, tiles, and other smooth flooring options, there are increasing problems with pets not being able to rise from a resting position and get traction while moving across these surfaces. This also leads to increased slipping and sliding on smooth-surface floors making dogs more prone to injuries and exacerbation of coexisting conditions. Pet owners are looking for options to help their pets, mainly elderly and those diagnosed with orthopedic conditions, have an improved quality of life. Immobility is often seen as a significant concern and a quality of life issue. Pet owners constantly worry about their pets being able to ambulate outside, get to food and water, and maintain mobility and muscle function.

As dogs age, they lose both muscle mass in their hind legs and the friction surface of their paw pads. This combination creates difficulty for elderly animals rising from a resting position and maintaining correct posture while moving and standing for extended periods of time. The options to decrease sliding and slipping are to increase either the downward force or increase coefficient of friction. The present invention increases friction by increasing the coefficient of friction. This product is applied directly to the pads of the paw so that the user determines how much of the product is applied and where the product is applied. This significantly increases the grip on the pad surface by creating a custom-fit friction-increasing product that is specific to that pet's paw surface, rather than having to use an item that has a mass produced, predetermined size, shape or volume. This custom fit, in turn, makes it much easier for a dog to get to a standing position and decreases both backward and lateral sliding of the front and hind legs. Quality of life is improved greatly because of the decrease in possible injuries, freedom of mobility, increased confidence, and the gain of muscle mass. This product and its method of use go beyond the scope of use just for elderly animals. It helps animals with any existing medical issues (orthopedic and neurologic included) that influence the mechanical ability of paw placement. It can also be used in younger pets that may need support while running or playing on slick surfaces.

For purposes of development, the term "friction" means dry friction or the lateral motion of two surfaces in contact. Increasing friction relies on either increasing the downward force of the object that is sliding (in animals this includes the downward force of the muscles upon the floor) or increasing weight. Unfortunately, weight increase in animals is associated with increasing debilitation of orthopedic and neurologic conditions and decreased length of life. Using the force formula, friction can be increased by increasing the coefficient of friction. This is a value that describes the ratio of force between two bodies.

An apparatus placed on a dog's foot, such as a boot or shoe, causes distress and discomfort when being wrapped or placed over the foot; is easily destroyed by the animal or wears down with chronic use in harsh environments. It can be ingested leading to foreign body obstruction and surgery, and can be associated with medical conditions such as pyoderma or dermatitis from humidity and dampness. It is often held in place by VELCRO® fasteners or other fastening devices. The fasteners weaken with the inevitable collection of dirt and debris from everyday use. Further these devices are not meant to be on the animal 24 hours a day, leading to times when the dog still has slipping issues when the devices are removed.

Individual products placed on toes or pads, such as adhesive-backed appliques or toe nail grips, are difficult to place as each individual piece is individually applied to ensure appropriate fit and adhesion. The sizing of the product is extremely important for proper fit. Different sizes are needed according to the size of the animal, and one size does not fit all. As a consequence, individual pieces can easily be lost or destroyed during normal use. The efficacy of the product relies on the sum of its individual parts. Finally, the Toe Grips™ product require an optimal length of a dog nail for support which can be very hard to achieve.

Chemical compounds that are applied to pads, such as waxes, sprays or lotions, are for very short term use and are used for instances when a dog needs immediate traction for performance, such as dock diving or walking a show ring. They wear off very quickly. Products are contaminated easily by whatever substrate the animal is walking on, thereby losing their effectiveness for gripping.

The present invention provides the necessary ingredients for the consumer to create a bonded, thin, high friction-coating on targeted areas of a dog's paw to create an immediate increase in traction. The method of applying the present invention is streamlined and needs minimal accuracy or technical skill. Prior sizing of the product is irrelevant as the adhesive is applied directly to each paw pad. There is no necessity of individual sizing options or anatomical requirements of the animal. The applied cured adhesive compound mimics the natural surface and geometry of a dog's paw pad. The friction enhancing property of the compound makes it effective even when a large amount of the product has rubbed off. The compound is safe if ingested by animal or people. Typically, the product is not noticed by the animal once it is applied.

The product is robust and holds up admirably against normal physical activity of the animal. The method of application lends itself to make the product multiple-use and multifunctional for traction control. The product addresses all forms of slipping including lateral, medial, cranial, and caudal.

Many prior art products have a supported surface such as an adhesive-backed pad with a roughened surface that is adhered to the pads of an animal paw. Such devices are disclosed in U.S. Pat. No. 8,468,978, WO2005082133, and U.S. Pat. No. 6,863,033. These devices have the disadvantage of too easily being peeled off by the animal when walking or running, or chewed off by the animal which instinctively cleans its paws. There is no prior art device or method that does what the present invention does.

Further examples of known prior art devices are described in U.S. Pat. No. 2,475,417, U.S. Pat. No. 3,762,073, U.S. Pat. No. 6,056,062, U.S. patent application 20140109842A1, and WO2014071462A1, which are hereby incorporated by reference.

SUMMARY OF THE INVENTION

The present invention comprises a cured adhesive having two sides, wherein adhered to one side is the pad of an animal's paw and adhered to the other side is solid particulates thereby increasing the friction of the pads. A method of increasing the friction of an animal's paw comprises applying to clean, dry pads of the animal's paw a layer of uncured adhesive, and while the adhesive layer is still uncured, pressing the paw with the adhesive into particulates to adhere the particulates to the adhesive, then curing the adhesive. A kit for increasing the friction of an animal's paw comprises a cyanoacrylate adhesive in a tube to dispense the cyanoacrylate polymer, rubber particulates, and a tray to contain the particulates.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 7 is a graph of the Differences in Temperature versus Time for the data shown in FIG. 6.

FIG. 8 is a graph of the Percentage Difference in Temperature versus Time for the data shown in FIG. 6.

DETAILED DESCRIPTION OF THE PREFERRED EMBODIMENTS

Figure 1:
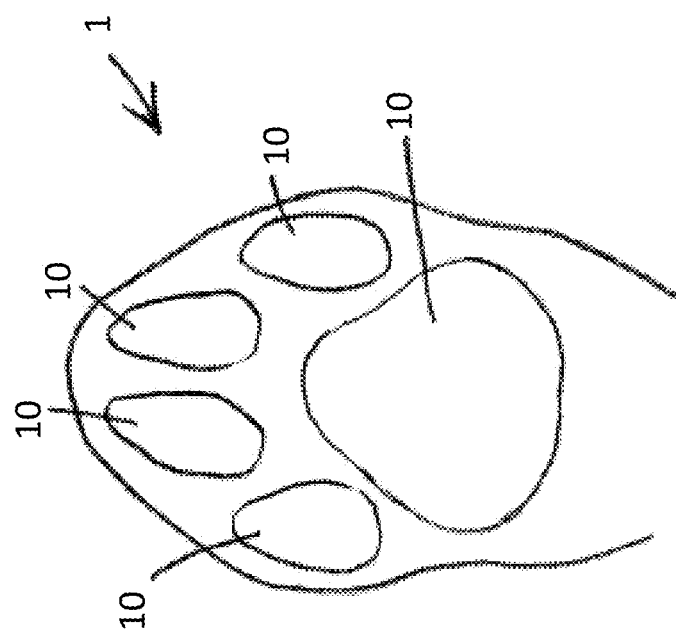
FIG. 1 is a bottom, plan view of a pet's paw with nothing adhered to the pads.

The following description of the preferred embodiment(s) is merely exemplary in nature and is in no way intended to limit the invention, its application, or uses.

The Adhesive:

A suitable adhesive is quick-bonding, strong, and non-toxic if ingested. The following types of adhesive were tested: 2-octyl cyanoacrylate, ethyl cyanoacrylate liquid and gel, and 60% 2-octyl and 40% N-butyl cyanoacrylate.

Based on the original results of testing, it was found that the ethyl cyanoacrylate performed the best; however, the 2-octyl-N-butyl cyanoacrylate formed a strong bond as well. Therefore, any cyanoacrylate is a sufficient adhesive for the present invention. In a preferred embodiment, a medical-grade adhesive is used. In another embodiment, any commercial or industrial grade cyanoacrylate would be used.

Ethyl cyanoacrylate comes in a large number of viscosities, many of which were tested, ranging from free-flowing liquid to paint-able gel. The preferred viscosity was about 1000 cps, but any stable cyanoacrylate would be suitable. A preferred range of viscosities is from about 200 cps to about 1000 cps. Viscosity affects both the bonding time and the ease of application. With greater viscosity, it is easier to direct the adhesive to the paw pad and not have it flow off the pad. Additionally, in a preferred embodiment, the adhesive would bond to the granular matter and cure in a matter of 60 seconds or less. All cyanoacrylates tested appeared to bond within that acceptable time frame. Curing time is critical when dealing with a mobile live animal, so the adhesive of the present invention has a fast curing time for ease of use.

Granulated Substrate Development

The granulated substrate is adhered to the paw surface. By increasing the coefficient of friction of the paw on a smooth wood surface, the substrate is the single component whereby we are able to increase friction in the paws of animals such as dogs and cats. The coefficient of friction is a dimensionless scalar value which describes the ratio of the force of friction between two bodies and the force pressing them together. The coefficient of friction depends on the materials used. For example, ice on steel has a low coefficient of friction, while rubber on pavement has a high coefficient of friction. Coefficients of friction range from near zero to greater than one. We looked at many substrates that would increase the coefficient of friction to the range of about 0.5 to about 1.3. We used the coefficient of friction of leather on smooth wood as our baseline because it most closely mimicked the appearance and feel of the surface of a worn paw pad, and a smooth wood surface is often what an animal is walking on.

Coefficient of Friction ($\mu$)

Leather on Wood: 0.3

Rubber on Wood: 0.9

Rubber on Asphalt: 0.6

Rubber on Concrete: 0.6-0.85

Car tire on Asphalt: 0.72

Hemp rope on Timber: 0.5

Based on trials and previously published coefficients of friction, granular rubber particulate substrate performed the best, providing an improved coefficient of friction. Additionally, particulate rubber was non-toxic, easy to obtain, and able to be formulated into a variety of sizes and shapes. Once the substrate was chosen, the next testing was to determine the particulate size of the rubber.

Rubber Particulate Size

Rubber particulates ranging from 0.00125 mm (manufactured product) to approximately 5 mm in size (cut individually from larger sheet) were tested. It was found that the use of rubber in any of the sizes tested would result in increased friction on paw pad surfaces. A smaller sized particulate had the desired property of not rubbing off easily. Additionally, it was obtainable in large amounts with quality assurance, and mimicked the original, non-worn surface of the animal's paw pad.

The first tested application method was to apply to the paw pads a pre-mixture of rubber particulates and adhesive at a set ratio. The pre-mix would be applied with a brush or acceptable application method to the surface of the paw pads. Testing showed that a pre-mix was unstable. Any exposure of the cyanoacrylate to air and humidity resulted in quick-bonding (curing) of the product. This reaction was intensified and accelerated when the rubber compound was introduced. Curing of the adhesive occurred when the particulates were added. Multiple stability experiments were made with different containers and environments such as plastic vs. glass and room temperature vs. freezing. An un-cured pre-mixed compound could not be made.

A new application process was developed using the ethyl-cyanoacrylate adhesive and a rubberized particulate. The liquid cyanoacrylate was stabile (uncured) for a small period of time when applied to a surface. The granulated rubber particles could be placed on the adhesive curing to form a very quick bond. The bonding was accelerated when pressure was applied from the adhesive to the granulated rubber. This pressure came from the paw being pressed into the rubber particulates.

Different application procedures of the adhesive were tested. The test included buying the adhesive in bulk and separating into smaller containers, applying the adhesive with brushes, applying the adhesives using brush-top bottles, and looking into individual small containers of adhesive. All tested methods had faults except for the individual bottles of adhesive. Any exposure of the adhesive to air again resulted in curing of the adhesive and some of the methods resulted in contamination of the adhesive with environmental contaminants. We ultimately decided on individual flexible sealed pipettes of adhesive to be discarded after each use. In a preferred embodiment, the pipette contains 1.0 mL of adhesive.

Packaging of Materials and Application Tray

Recognizing that the particulates would need to be placed in a structure/reservoir for the application process, a reservoir tray was designed that optionally could also serve as functional packaging for the process. A non-porous tray was evaluated. However, non-porous surfaces actually posed a danger to the animals during use. If cyanoacrylate adhesive came into contact with any non-porous surface, it bonded very quickly. This bond is as strong as what is seen with the granular matter and is difficult to remove. Removal of a non-porous, non-degradable product can be dangerous to the paw pad surfaces of the animals.

Other packaging options were pursued and a tray that is easily broken down or torn apart was developed. The tray was made with a porous, biodegradable paper-pulp product. These are made with recycled paper pulp compressed into a form. If the paw pad is accidentally glued onto the tray, the tray can easily be torn without any damage to the paw pads. The pulp left on the paw pad will wear off over a short period of time. Paper pulp is also non-toxic and environmentally friendly. The kit in a package contains the adhesive in sealed plastic pipettes, the rubber particles and the porous tray.

Application Instructions, First Embodiment

1. The nails are trimmed short enough that they cannot be heard contacting the ground. The hair around the paw pads is shaved and the pads are free from any dirt and debris.

2. The particulate/adhesive combination is best applied with a dog or animal in a supported standing position. This may require two people. If the dog cannot stand for long periods, please see the alternate instructions below.

3. One container of particulates is added to the tray. The tray is shaken to ensure adequate distribution of the particulates so as to cover bottom of the tray.

4. One end of the sealed plastic pipette containing the medical-grade adhesive is cut at a 45 degree angle using any standard pair of scissors.

5. Starting with one of the back paws, the foot is lifted backwards and the paw flipped up to show the pads.

6. The adhesive is applied to the surface of the paw pads by squeezing firmly on the adhesive pipette with the flat part of the cut pipette in contact with the pad surface. Getting any adhesive on the hair surrounding the pads should be avoided.

7. Once the pads are coated, the paw is inverted downward and placed into the particulates. Pressure is applied. The entire paw should be inside the tray. Pressure is applied for 1-10 seconds.

Optional Pre-Steps

There was variation of the lasting time of the product on paw pads. This may be attributed to application differences and a fair amount of organic debris on the paw pads disrupting the adhesive bond to the surface of the paw pads. The application process had been adapted to include the following pre-steps to increase the lasting time of the coating.

1. The paw pads are filed using a nail file or emery board. This disrupts and removes any organic material that may have collected in the keratinized surface of the paw pads. Studies comparing preparation of the paw pads in this manner have lengthened the time to the next application.

2. Either post-filing or before application in general, the paw pads are cleaned with isopropyl alcohol. In a preferred embodiment, a 50% or stronger solution of isopropyl alcohol is used to remove any superficial organic debris or chemicals.

3. The paw pads are allowed to dry completely before application of the product is commenced.

A Second Embodiment of Applying the Invention

Following the same instructions above for preparation and application of the adhesive, instead of placing the paw into the particulates, the particulates may be sprinkled onto the surface of the paws. Alternatively, the particulates may be placed into the tray and the tray pressed sideways onto the paw pads.

Either of the second embodiment processes will likely result in spillage of the particulates. The spillage may be gathered and placed back into the enclosed containers to be used again.

Figure 2:
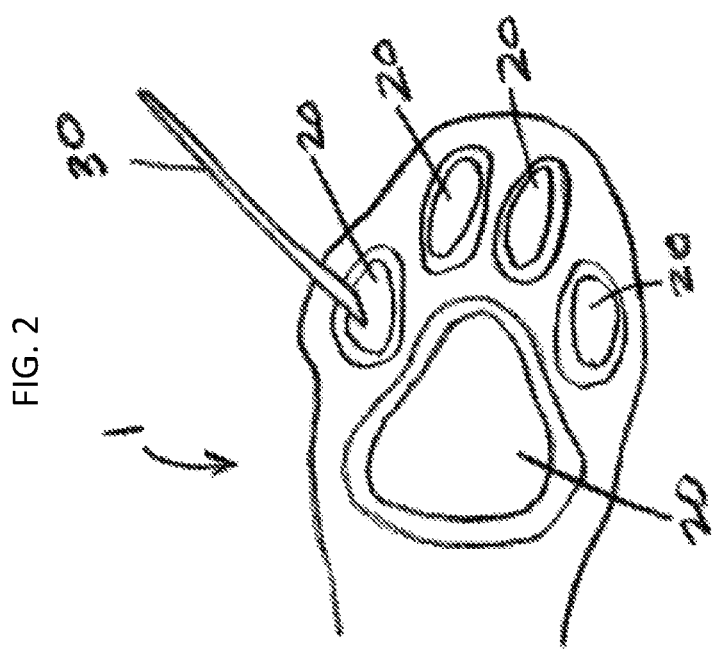
FIG. 2 is a bottom, plan view of a pet's paw with adhesive applied to the pads.
Figure 3:
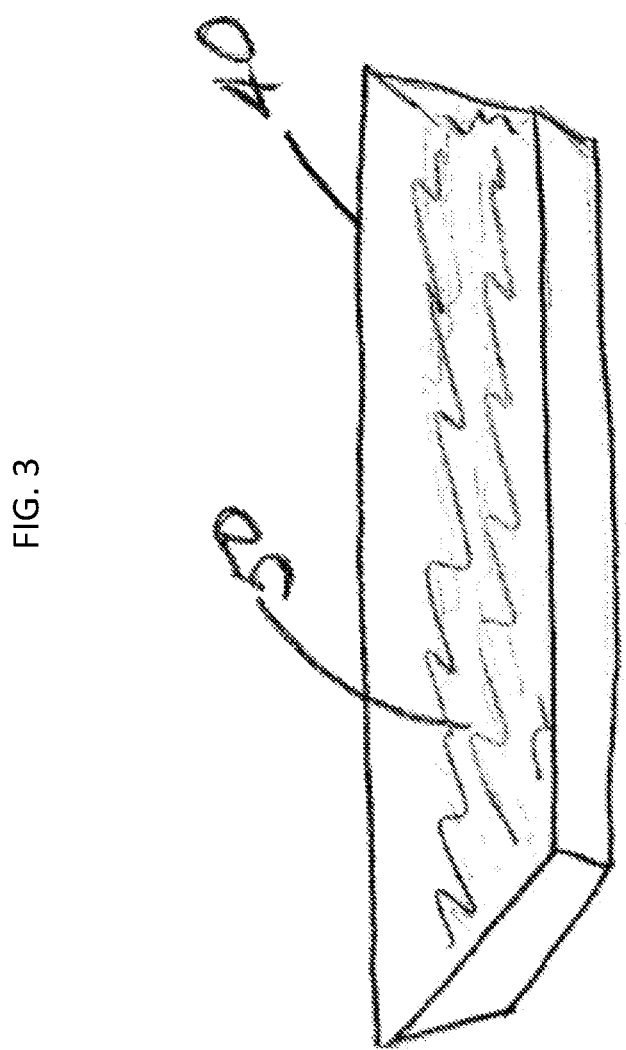
FIG. 3 is a perspective view of the tray containing granulated particles.
Figure 4:
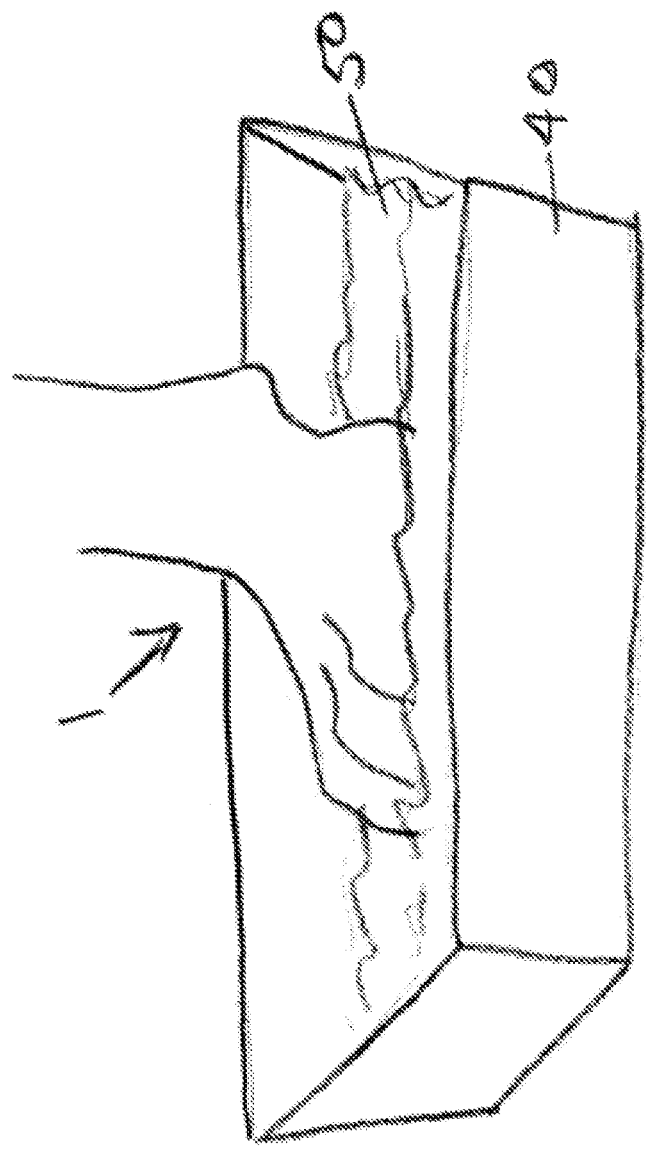
FIG. 4 is a perspective view of a pet's paw pressing down into the granulated particles.
Figure 5:
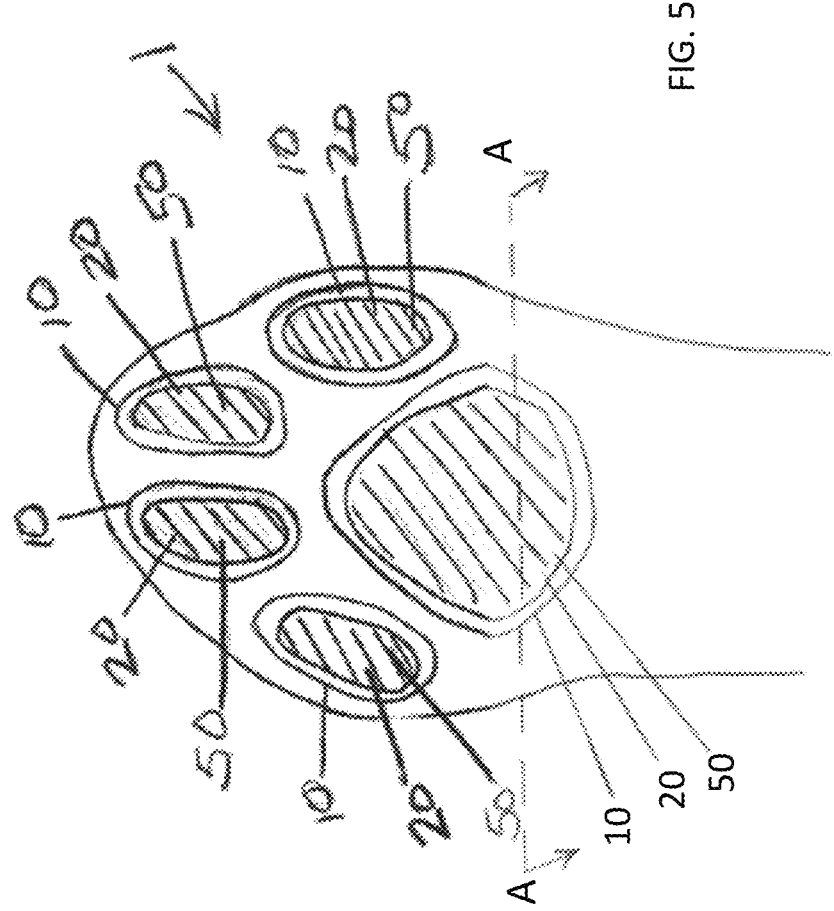
FIG. 5 is a bottom, plan view of a pet's paw with particulates adhering to the pads of the paw according to the present invention.
Figure 5A:
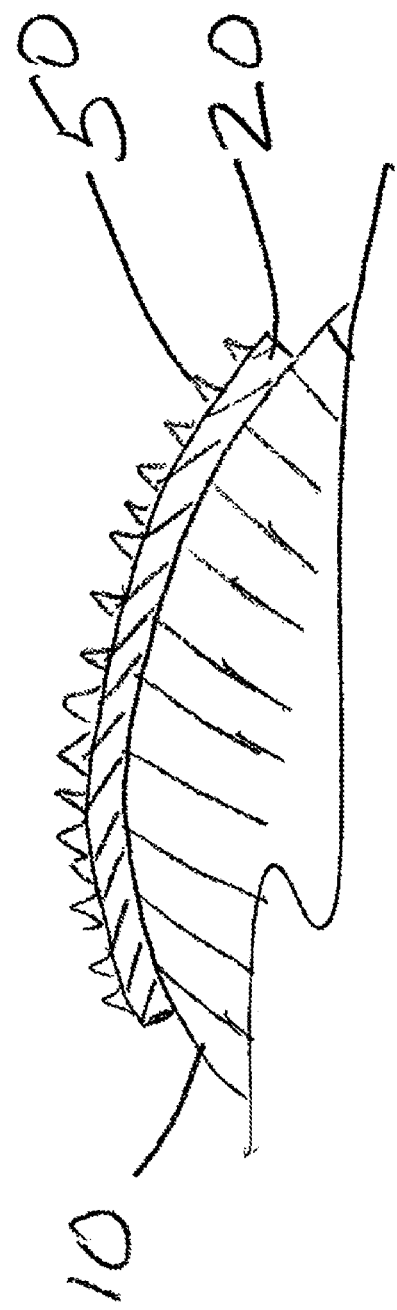
FIG. 5A is a cutaway view of FIG. 5 at A-A.

The first embodiment of the application procedure is disclosed in FIGS. 1-5. In FIG. 1, the paw 1 is held and the pads 10 are turned up. FIG. 2 shows a container 30 of adhesive that has been cut at a 45 degree angle is used to apply adhesive 20 to the pads. FIG. 3 shows the particulates 50 added to the tray 40 and shaken to spread out and cover bottom of the tray. In FIG. 4 the paw 1 is pressed into the particulates 50 in the tray 40 to adhere to the adhesive. In FIG. 5 the paw is withdrawn from the tray and the particulates have adhered to the adhesive 20 on the pad 10. The adhesive has now cured. FIG. 5A shows a cutaway view of FIG. 5 at A-A showing the two sides of the cured adhesive. In this manner, the friction is increased for the paws of the animal.

The present invention has been found to increase traction on ice as well as on smooth flooring. An additional use is as an adjunctive veterinary medical treatment device. With age, orthopedic, and neurologic diseases muscle atrophy becomes an increasing concern. With loss of the traction surface of the paw pads often dogs are unable to get the traction to hold themselves in place appropriately and keep the muscle mass healthy. Disuse atrophy leads to increased difficulty with mobility and results in a cyclical downgrade in the quality of life of pets. By increasing the traction surface of all four paws, isometric forces are created. The resulting isometric exercise keeps the muscle masses in a state of contraction leading to decreased loss of muscle mass as aging occurs. This could be a valuable tool for treating neurodegenerative and muscular degenerating diseases.

Another use is as a veterinary surgical assistance device. In the peri-operative setting, especially with orthopedic and neurologic surgeries, the risk of injury is heightened because of abnormal placement.

Another use is as a rehabilitation aid. Rehabilitation is becoming a large sector of the veterinary industry. By increased traction and isometric forces, rehabilitation becomes much more effective and improves the quality of life of the dogs.

Another use is to provide heat protection of the paw pads. It has been postulated that since that the main component that increases the friction is rubber that, when applied correctly, the rubber could pose some protection against high temperature surfaces when walking. Rubber has a thermal conductivity of 0.14-0.15 W/mK at 25 degrees Celsius. The temperature at which damage to the paw pads can occur is about 180 degrees F. For testing purposes a pavement/asphalt/concrete temperature of over 120 degrees F. is determined as a temperature which it would be dangerous to walk a dog on. The limit of 180 degrees F. because of the burning of the animal's paws. Because dogs do not have consistent contact of their paw pad surfaces to the ground by the nature of walking, the time of contact, pressure, and stride length are variable across each individual breed and would be very difficult to test. For purposes of testing, we opted to use constant contact across a surface realizing the temperature dampening effects would likely be greater during the normal stride of a dog.

Thermal Testing:

The thermal insulation capabilities of the present invention at a high temperature surface compared to a control. In order to complete this experiment, a test washer was prepared by applying cyanoacrylate adhesive to one side of a steel washer. Rubber particulates were applied to the adhesive and cured in the same manner that it would be applied to a dog's paw pads. An identical steel washer was left uncoated to act as a control. Both washers were placed on a hot plate on the lowest temperature setting at the same time. The coated side of the test washer faced down. Thermocouples were pressed against the uncoated top of each washer for 15 minutes and the temperature of each was recorded every 30 seconds for the entire 15 minutes. It was found that the test washer maintained a cooler temperature than the control washer throughout the entire test period. These results mean that the coating of the present invention may protect a dog's paw pads for a brief period of time from burning on hot surfaces during the summer months. The coating remained intact after the test without melting or peeling off and only suffered from a mild discoloration.

Figure 6:
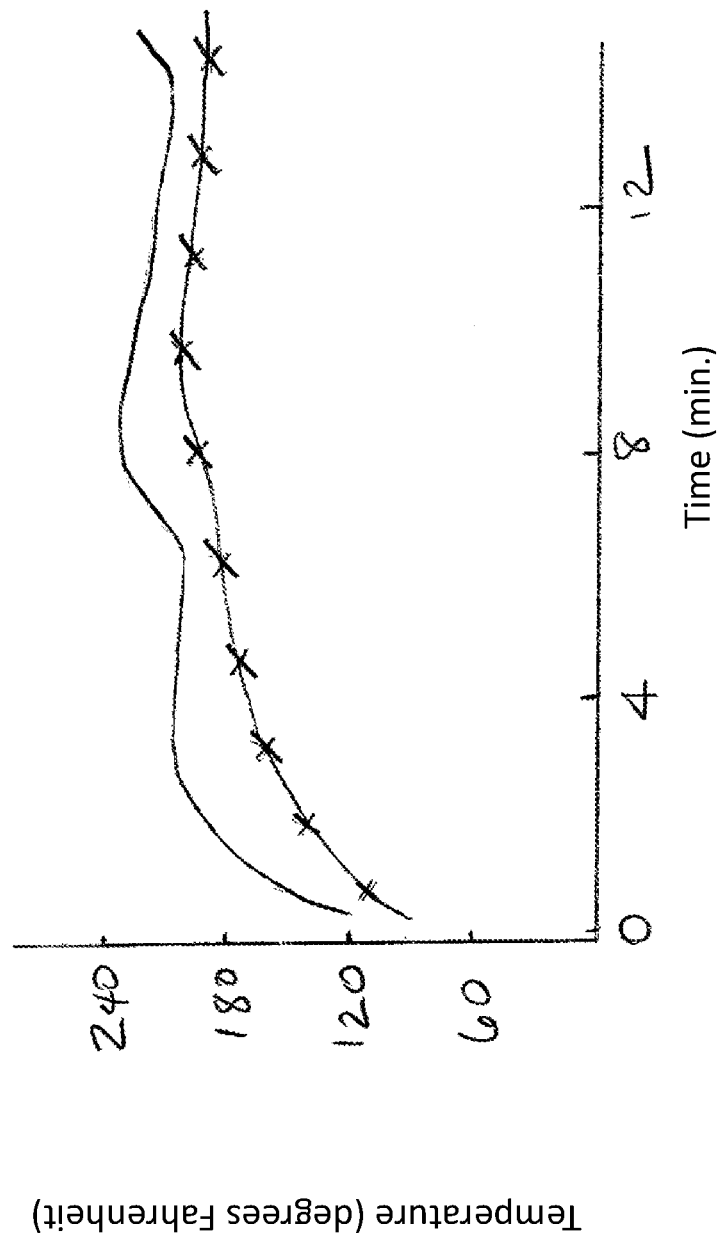
FIG. 6 is a graph of Temperature versus Time for a coated washer (test) and an uncoated washer (control).

The results of the thermal testing are given in FIGS. 6, 7 and 8. At lower temperatures, there was a significant difference in the temperatures of the test (coated) steel washer and the control (uncoated) washer. The control washer heated up to a hazardous temperature (118 degrees F.) within 0.5 minutes and exceeded the 180 degree F. cutoff (188 degrees F.) within 2 minutes. The coated test washer exceeded 120 degrees F. (129 degrees F.) at 1.5 minutes and exceeded 180 degrees F. (181.8 degrees F.) at 7.5 minutes. There is a significant difference that could lead to decreased injury during walks on hot surfaces. The longer the washers were in contact with the heat source, the less the difference of the temperatures of the washers. However, the coated washer was consistently cooler than the control and provided protection when walking on hot surfaces.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of increasing the friction of an animal's paw comprising
 a) applying to a clean, dry pad of the animal's paw a layer of uncured adhesive;
 b) contacting the uncured adhesive with granulated particulates, and
 c) curing the adhesive;
 wherein the granulated particulates are rubber particulates;
 wherein said uncured adhesive is an ethyl cyanoacrylate adhesive;
 wherein the uncured adhesive and the rubber particulates are not premixed; and
 wherein the friction of the paw is increased.

2. The method of claim 1 wherein the adhesive is an ethyl cyanoacrylate having a viscosity of from about 200 to 1000 cps.

3. The invention of claim 1, wherein the animal's paw is pressed onto a tray containing rubber particulates to contact the uncured adhesive with the rubber particulates.

4. The invention of claim 3, wherein the rubber particulates are poured over the animal's paw to contact the uncured adhesive with the rubber particulates.

5. The method of claim 3, wherein before applying the uncured adhesive, the animal's paw pad is cleaned using a file.

6. The method of claim 5, wherein after the animal's pad is cleaned with a file, the pad is washed with isopropyl alcohol.

7. The method of claim 6, wherein the isopropyl alcohol has a concentration of at least 50%.

8. The method of claim 7, wherein the paw pad is thoroughly dried before applying the adhesive.

9. A method of protecting an animal's paw pad from excessive heat damage comprising:
 a) cleaning the paw pad by filing;
 b) washing the paw pad using isopropyl alcohol;
 c) drying the paw pad thoroughly;
 d) applying to a clean, dry pad of the animal's paw a layer of uncured adhesive;

e) contacting the uncured adhesive with granulated particulates, and f) curing the adhesive;

wherein the granulated particulates are rubber particulates;

wherein said uncured adhesive is an ethyl cyanoacrylate adhesive;

wherein the uncured adhesive and the rubber particulates are not premixed; and wherein the paw pad is protected from excessive heat damage.

10. The invention of claim 9, wherein the animal's paw is pressed onto a tray containing particulates to contact the uncured adhesive with the rubber particulates.

11. The invention of claim 9, wherein the rubber particulates are poured over the animal's paw to contact the uncured adhesive with the particulates.

12. The method of claim 9 wherein the adhesive is an ethyl cyanoacrylate having a viscosity of from about 200 to 1000 cps.

* * * * *